United States Patent

Batista

[11] Patent Number: 5,807,997
[45] Date of Patent: Sep. 15, 1998

[54] METHOD FOR IMMOBILIZATION OF THIOL COMPOUNDS VIA ACTIVATION OF POLYMERS, ACTIVATED POLYMERS, AND PRODUCTS OBTAINED BY THE METHOD

[76] Inventor: Francisco Batista, Gauna 3798 bis, Montevideo, Uruguay

[21] Appl. No.: 813,868

[22] Filed: Dec. 20, 1991

[30] Foreign Application Priority Data

Dec. 19, 1990 [SE] Sweden .................................. 9004047

[51] Int. Cl.$^6$ .............................. C07K 16/00; C07H 1/00; C08B 11/00; C08F 8/00
[52] U.S. Cl. ...................... 530/362; 530/350; 530/391.1; 530/391.3; 530/391.5; 530/391.7; 530/391.9; 530/402; 530/404; 530/408; 525/61; 536/1.11; 536/92; 435/180
[58] Field of Search ..................................... 530/392, 350, 530/391.1, 391.3, 391.5, 391.7, 391.9, 402, 404, 408; 536/1.1, 92, 1.11; 525/61; 435/180

[56] References Cited

U.S. PATENT DOCUMENTS

| | | | |
|---|---|---|---|
| 4,175,073 | 11/1979 | Axen et al. ............................... | 526/303 |
| 4,558,006 | 12/1985 | Egrie ........................................... | 435/7 |

FOREIGN PATENT DOCUMENTS

A-63109   10/1982   European Pat. Off. .
A-363192  4/1990   European Pat. Off. .

OTHER PUBLICATIONS

MacLaren et al.—Aust. J. Chem., 18(1965) 1655–65.

MacLaren et al—J. Soc. Dyers and Colourists, (1968–11) 564–67.

Rajca et al—Tetrahedron Letters, 31 (1990) 42 A pp. 6075–6076.

*Primary Examiner*—Christina Y. Chan
*Attorney, Agent, or Firm*—Dinsmore & Shohl LLP

[57] ABSTRACT

A method for the immobilization of an organic thiol compound, HS—R, in which R is an organic residue, to a water-insoluble polymer of non-polypeptide structure exhibiting a disulfide (—S—S—) group directly bound to a saturated carbon atom at each of its sulphur atoms, which comprising contacting the polymer with an oxidation agent in such an amount and of such a kind that it is capable of transforming the disulfide group (—S—S—) to an oxidized disulfide group capable of reacting with thiol groups, whereupon the polymer obtained exhibiting one or more oxidized disulfide groups is contacted with the organic thiol compound HS—R under conditions allowing reaction to the formation of one —S—S—R group and one —SO$_n$(H) group per disulfide oxide group that undergoes the reaction, where n is 1 or 2.

20 Claims, No Drawings

METHOD FOR IMMOBILIZATION OF THIOL COMPOUNDS VIA ACTIVATION OF POLYMERS, ACTIVATED POLYMERS, AND PRODUCTS OBTAINED BY THE METHOD

The present invention relates to a method for the covalent binding of an organic thiol compound (HS—R) to a polymer exhibiting one or more organic disulfide (and/or thiol) group(s).

The disulfide group in an organic disulfide is linked to a carbon atom at each of its sulfur atoms. The expression polymer is to be construed in a broad sense. Hence proteins and other macromolecules in which the repetitive units are different are within the scope of polymer as used in this invention.

The main use of the present invention is within the biotechnological field such as biochemistry, biomedicine, medicine, purification of aqueous liquids, e.g. in connection with fermentation, and similar fields related to biotechnology. The invention does not relate to chemical modification of wool textile fibres.

The method of the present invention is particularly adapted for preparing covalent conjugates of two or more compounds where at least one of the compounds has a polymeric structure (=polymer) and normally function as a carrier for the other components of the conjugate. Important conjugates make use of soluble and insoluble biopolymers, such as proteins including polypeptides (e.g. albumin, globulins such as antibodies, antigens etc.), polysaccharides and nucleic acids, and soluble and insoluble synthetic polymers. Particularly interesting conjugates involves compounds that participate in biospecific affininty reactions, e.g. antibodies and antigens/haptens, and solid supports used in immunosorbent and other biotechnological contexts.

In organic synthetic chemistry it has since quite a long time been known that aliphatic and aromatic disulfides ($X_2$—S—S—$X_3$) may be split oxidatively in their C—S or S—S bond; with the predominant route being cleavage at the S—S bond giving sulfonic acid groups (R—$SO_3^-$) in the final product. Suggested intermediates have contained —$SO_n$—$SO_m$— groups, where n and m=0, 1 or 2 with at least one of them being >0. The reaction has been performed in order to solubilize proteins. Performic acid has been used for selective splitting in cysteine residues in order to investigate the primary structure of proteins. Within the textile industry, it has been suggested that oxidized forms of —S—S— in wool textile fibres could be used for covalently linking a desired molecule to the fibres. See for instance MacLaren et al. (J.Soc.Dyers and Colourists (1968) pp564–67 and Aust.J.Chem. 18 (1965)pp1655–65).

Disulfide and thiol groups have found an increased use in the preparation of conjugates in which bio-organic compounds are involved. The most important reactions fall under the general concept thiol-disulfide exchange reactions

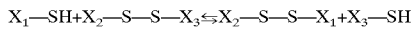

$X_1$—SH+$X_2$—S—S—$X_3$⇌$X_2$—S—S—$X_1$+$X_3$—SH

In the scheme $X_1$, $X_2$ and $X_3$ are organic residues having a saturated or an unsaturated carbon atom next to each of the sulfur atoms. In the contexts of conjugate preparation reactions of disulfides with thiols have been of great value because they can be performed selectively under mild conditions (aqueous milieu, neutral pH) without concomitant reactions of other nucleophilic and/or electrophilic groups.

The disadvantages of the prior art conjugating methods employing HS—/—S—S— groups have differed from case to case depending largely on the types of molecules to be conjugated. A common drawback has been that a thiol-disulfide exchange reaction always releases $X_3$—SH that normally has to be removed before further use of the conjugate produced, The presence of organic thiols may initiate thiol/disulfide mediated rearrangements in polydisulfides.

It is an advantage to be able to perform coupling by formation of disulfide groups without release of any thiol compounds ($X_3$—SH). The present invention solves this problem.

One aspect of the invention is a method for immobilizing an organic thiol compound, HS—R, to a polymer exhibiting one or more (=at least one) disulfide (—S—S—) groups. R is an organic residue providing a carbon atom ($C_1$) that is attached directly to the sulfur atom (S) of HS—R. This $C_1$ carbon atom is preferably saturated (sp³-hybridized). Each of the sulfur atoms of the disulfide group(s) is directly attached to saturated carbon atoms that are comprised within the polymer ($C_2$ and $C_3$, respectively; sp³-hybridized). The characteristic feature of this aspect of the invention comprises the steps of (i) Contacting said polymer with an oxidizing agent in such an amount and of such a kind that is capable of transforming said disulfide group (—S—S—) to an oxidized disulfide group that is capable of reaction with organic thiol groups, said binding between the carbon atoms ($C_2$ and $C_3$ provided by the polymer) and the sulfur atoms being maintained during the oxidation and said oxidized disulfide preferably being a disulfide oxide such as a —S—$SO_n$— group, where n is 1 or 2, (ii) Contacting the polymer obtained in step (i) and exhibiting one or more oxidized disulfide groups with the organic thiol compound HS—R under conditions allowing a chemical reaction to the formation of one —S—S—R group and one —$SO_n$(H) group per disulfide oxide group that undergoes the reaction.

During step (ii) the sulfur-carbon bonds (S—$C_1$, S—$C_2$ and S—$C_3$) involved remain unbroken. For n equals 1, —$SO_n$(H) will become —SO(H), that may react further with thiol compounds, R'—SH, to —S—S—R' and $H_2O$. R' may be equal to R. Above (H) indicates that —$SO_n$(H) are acidic groups that can exist as bases (ionic groups).

The definition of the preferred oxidized disulfide groups is based on the interpretation of our experimental results proposing as activated structures thiolsulfinate and/or thiolsulfonate. However, the invention is not limited to this interpretation but is also covering other activated structures which comply with the obtained results.

The polymers referred to above are different disulfide-carrying polymers that may be essentially of three major types—inorganic polymers, biopolymers and synthetic polymers, the difference between them being related to an inorganic, a biological or a synthetic origin, respectively, of the chain of the repeating basic units (basic polymer skeleton), this definition means that derivatized biopolymers are classified as biopolymers. Polymers exhibiting all three types of skeletons can be classified into any of the major types. Examples of synthetic basic polymers are poly(meth) acrylates, such as polyhydroxy(meth)acrylates, polyvinylalcohols, poly(meth)acryl amides etc and derivatives thereof. Examples of biopolymers are polysaccharides, such as dextrans, agarose, starch etc, that may or may not be synthetically derivatized.

In case the polymer lacks disulfide groups or thiol groups these groups normally can be introduced by methods known in the art by the use of commercially available thiolating reagents, e.g. bifunctional reagents carrying either a thiol or a disulfide group. The literature is extensive with respect to suitable reagents that in addition to a thiol/disulfide group carry the appropriate activated nucleophilic or electrophilic group for reaction at a electrophilic or nucleophilic group, respectively, in the polymer. As long as the basic polymer exhibits functional nucleophilic groups, such as alcoholic and phenolic hydroxy (HO—), carboxy (HOOC—), amino ($H_2N$—) or corresponding groups in activated forms (=electrophilic groups) there should not be any problem.

In case the polymer exhibits one or more thiol groups these can be oxidized to disulfides by per se known methods. Examples of suitable agents are potassium ferricyanide and air in the presence of cupric ions and a slightly alkaline milieu etc. Peroxides can also be used but then it is difficult to stop the reaction at the disulfide stage. Often the oxidation proceeds to the disulfide oxide or sulfonic acid stage.

The reactions utilized in the invention may be applied to both water-soluble and water-insoluble polymers of the type given above. In particular insoluble polymers of non-polypeptide structure, such as different chromatographic supports or supports used in other biotechnological contexts may be used The disulfide group of the polymer may be of intra- or interchain type. In case two polymer chains only are linked together by disulfide groups that are cleaved in the present immobilization method, the chains will become released from each other giving two molecular entities.

The oxidation step is performed by bringing the polymer containing the disulfide bond in contact with the oxidation agent. The main criterion is that the agent and the conditions applied should not give significant damages on the polymer or unwanted changes of the disulfide groups. Depending on the polymer the choice of oxidation agent and conditions applied are more or less important. For instance, polymers being relatively inert towards oxidation (as poly(meth) acrylates) may allow large excesses of strong agents. On the other hand polymers exhibiting groups easy to oxidize may require weak agents and/or equimolar amounts. Examples of groups that may be oxidized in competition with disulfide bonds are primary and secondary alcoholic groups, such as in polysaccharides, indolyl groups, thioeter groups etc. In particular it is known that proteins and polypeptides needs separate care because of the presence of several sensitive groups. Hence the use of $H_2O_2$ might in some cases not work and the use of other strong oxidative agents such as peracetic acid and performic acid may lead to undefined products and denaturation. Besides cysteine and cystine residues, performic acid can also oxidize methionine and tryptophan residues in proteins, and under very harsh conditions also tyrosine, serine and threonine residues.

The oxidation agent is selected amongst those that per se are known to oxidize disulfides, such as peroxides and metaperiodate. Among the peroxides inorganic as well as organic peroxides may be used if they are paired with the appropriate substrate (polymer). Peroxides carry the common structure —OO—. The inorganic ones normally comply with the general formula X—OO—X' where X and X' is selected among hydrogen or metal ions. Examples of organic peroxides are dihydrogen peroxide ($H_2O_2$) natal hydrogen peroxide and di metal peroxide. In aqueous media the presence of the different forms varies with pH and addition of metal ions. The organic peroxides comply with the same formula X—OO—X' but with the exception that at least one of X or X' is an organic residue that provides a carbon atom attached directly to the peroxy group (—OO—). This carbon atom may be saturated such as in alicyclic peroxides or a carbonyl carbon atom as in carboxylic peroxy acids (—CO–OO—).

We have found that there exist oxidation agents that essentially quantitatively in the presence of equimolar amounts oxidizes a disulfide group to the corresponding thiolsulfinate group (n=1), and then by addition of more oxidation agent takes the thiolsulfinate group to a thiolsulfonate group (n=2). In particular carboxylic peroxy acids carrying a carboxy group at a distance of two or three carbon atoms from the carbonyl carbon of the —CO—OO— group and/or an aromatic ring (e.g. phenyl or phenylene) bound to the same carbonyl carbon are potentially very usable. The carboxylic peroxy acid may for instance be in the form of a metal salt. With the present knowledge the magnesium salt of monoperoxy o-phtalic acids (two moles monoperoxy phtalate per mole $Mg^{2+}$) is the preferred agent. What has been said in this paragraph does not exclude that these peroxy compound can be used for oxidations from the thiol/disulfide stage directly to any of the two disulfide oxides(n=1 or 2) or that other salts can be used. Moreover under the proper conditions, these agents can be used in order to oxidize disulfide bonds in proteins (polypeptides).

The pH of the oxidizing medium is critical, Too high and too low pH will lower the yield, probably due to competing reactions. For aqueous media the optimal pH-range normally is within 3.5–7.0.

By selecting the proper oxidation agent and proper condition, step (i) can be selectively stopped at stages where n=1 or 2. Too drastic oxidation conditions (time, concentration, temperature etc.) will result in overoxidation appearing as cission of —S—S— and/or C—C bonds and loss of reactivity with thiol groups. For optimization see the experimental part.

In aqueous media step (ii) is performed at pH-conditions where the product of step (i) (polymer containing thiolsulfonate and/or thiolsulfinate groups) is hydrolytically stable while simultaneously allowing for reaction with HS—R. In actual praxis this means aqueous media and pH within the range 6–9.

The compound HS—R may be any organic thiol compound provided that it, except for reaction at the thiol group, is inert during the conditions applied in step (ii). In case the method of the invention is utilized in the preparation of conjugates, HS—R is selected in accordance with the properties desired to be linked to a given polymer. HS—R may be a compound participating in biospecific affinity reactions, such as a thiol-containing antigen/hapten, antibody/antibody active fragment, lectin, carbohydrate (soluble carbohydrates such as dextrans, carboxymethyl cellulose, etc.), Fc-portion of IgG, Protein A or G etc. It may be analytically detectable (radioactive, fluorescent, chemiluminescent, enzyme active such as a substrate, a coenzyme, a cosubstrate, a substrate etc), an insoluble polymer that may be of the same type as the polymeric compound carrying the disulfide bond and so on. However, this does not exclude that HS—R may be other compounds, e.g. thiol-containing contaminants. Surprisingly, it has been found that even thiol compounds stabilized by thiol-thione tautomerism to corresponding thioneforms may react, e.g. compounds in which the thiol group binds directly to a $sp^2$-hybridized carbon atom that is part of a heteroaromatic ring or part of an aromatic ring substituted with electron-withdrawing substituents. In case a certain compound does not contain a thiol group, the group normally can be introduced by methods known in the art, see above.

In particularly important modes of this aspect, HS—R is a bio-organic substance.

A second aspect of the present invention is the intermediary product obtained in step (i). In this aspect the polymer carrying the disulfide oxide group is preferably insoluble in aqueous media. With respect to the major type of polymeric base skeleton the polymer may be of any type, although nucleic acids and per se insoluble polypeptides (proteins) in connection with the biotechnological field are normally not suitable.

The preferred mode of the second aspect of the invention is a water-insoluble support that can be used for the insolubilization of a thiol-containing compound (HS—R) of the type given above. The characteristic feature of the support is that it exhibits a plurality of —S—SO$_n$— groups, the sulfur atoms of which are attached directly to saturated carbon atoms. n=1 or 2. The content of —S—SO$_n$— groups is normally within the range of 20 . 1500, preferably 50–500, μmoles/gram dry support (based on the capacity of the support to react with an excess of reduced glutathione according to the method described in the experimental part). Theoretically for n equals 1 the thiolsulfinate group may react with two equivalents of thiol groups. In such cases the thiolsulfinate content is obtained by dividing the measured glutathione binding capacity with two.

The polymer of the insoluble support comprises polymers that are water-insoluble as such but also water-soluble polymers that have been rendered insoluble by being physically adsorbed, covalently bound or otherwise attached to the surface of a support that is insoluble in an aqueous media are included. For specific polymers see above. The support of this aspect may have different physical forms, such as beads that may be porous or homogeneous, the walls of a microtiter wells, slides, foams, sticks, etc. Particularly interesting are polymers that are used as supports (stationary phases) in liquid chromatography. Examples of such supports are beaded agarose (SEPHAROSE, Pharmacia AB, Sweden); crosslinked dextran (SEPHADEX, Pharmacia AB, Sweden), polyacryl amide (EUPERGIT, Rohm-Haas, West-Germany). In this aspect of the invention wool textile fibres are excluded as the polymer (support).

The support of the invention may be used for the insolubilization a thiol-containing organic compound (HS—R) dissolved in an aqueous fluid. R has the same meaning as above. This use comprises the step of contacting HS—R, dissolved or suspended in an aqueous fluid, with the insoluble support as previously defined. The conditions are the same as those given for step (ii) above.

The support of the invention may be employed for the removal of thiol compounds from aqueous solutions (e.g. for purification purposes), covalent chromatography involving reversible insolubilization of bio-active compounds, preparation of affinity adsorbents carrying a covalently attached thiol-containing compound exhibiting biospecific affinity.

After use the support can be regenerated by treating it with a reducing agent, such as excess of thiol compounds, and oxidation of the formed support-bound thiol groups to disulfide and disulfide oxide groups in accordance to what has been described above. In case the support carries —S—SO$_2$— groups the capacity for binding thiol compounds will decrease 50% for each regeneration cycle (the missing 50% appearing as —SO$_2^-$ or —SO$_3^-$ groups). For supports carrying —S—SO— groups no significant loss of capacity needs to take place for each cycle.

A third aspect of the invention is novel products that can be obtained by use of the present invention. These products consist of a polymer carrying both —SO$_n$(H) and —S—S—R groups where n equals 1 or 2, (H) indicates that —SO$_n$(H) is an acid group that can exist as a base (ionic form), and each of the free valences of the sulfur atoms is binding directly to a saturated carbon atom. Preferably the groups are present in essentially equimolar amounts. —S—R corresponds to HS—R defined for step (ii) above and has the same meaning. Suitable polymers are also the same as defined previously.

The invention is further defined in the appending claims being a part of the specification.

EXPERIMENTAL PART

Analytical Procedures

All analyses were performed on gel and gel derivatives that had been dried to constant weight over $P_2O_5$.

Thiol group content: This was determined spectrophotometrically as capacity to react with 2,2'-dipyridyl disulfide (=2-PDS) (Brocklehurst et al. Biochem. J. 133(1973) p573–8).

Disulfide oxide (—S—SO$_2$— and —S—SO—) contents: These were determined as capacity to bind reduced glutathione. Suction dried gels (2.5–3.0 g) were equilibrated in sodium phosphate (pH 7.0, 0.1M). Glutathione (3.0 mL, 15 mM) in the same buffer was added and incubation performed for 30 min at 22° C. while mixing every fifth minute. A blank for spontaneous oxidation of glutathione was run by replacing the gel with an equal amount of phosphate buffer. After centrifugation, aliquots of the supernatant and blank (50 μL) were mixed with 2-PDS (3.0 mL, 0.25 mM in sodium phosphate (pH 8.0, 0.1M)). The absorbance of the mixture was then measured at 343 nm. The amounts of glutathione which bound to the oxidized gels were calculated from the difference in absorbance readings at 343 nm between the supernatants for the glutathione blank and the gel derivatives using the molar extinction coefficient for thiopyridone.

Sulfur and amino acid analyses: Sulfur analyses were performed according to standard procedures on dried gel products (thiol and disulfide polymers, activated polymers and final conjugates before and after treatment with reducing agent). Amino acid analysis was performed with polymer-glutathione and polymer-protein conjugates before and after treatment with reducing agent.

Thiol Polymers

Preparation of thiol agarose: Mercaptohydroxypropyl ether agarose gel (thiol agarose) was prepared by a three-step method (Axén et al. Acta Chem.Scand.B 29(1975) pp471-) involving treatment of agarose with epichlorohydrin, sodium thiosulfate and dithiotreitol (DTT). By varying the relation between epichlorohydrin and agarose, products containing from a few up to 1,000 μmoles HS-groups per gram dried product ware obtained. 2.5 mL of epichlorohydrin per 15 g suction dried SEPHAROSE 4B (agarose, Pharmacia AB, Sweden) gave a product containing 500–700 μmoles per gram dried product.

Thiolation of other polymers: Beaded cellulose, SEPHADEX G-75 (crosslinked dextran; Pharmacia AB, Sweden), and EUPERGIT (epoxy activated polyacryl amide; Rohm Pharma GmbH, West-Germany) were thiolated by the same method as agarose.

Agarose and the polymers previously mentioned were also thiolated by a two-step procedure involving reaction with epichlorohydrin and a subsequent treatment of the gel-bound oxirane groups with NaSH at high pH.

Disulfide Polymers

Disulfide gel 1: 15 g of suction dried thiol agarose was suspended in 45 mL of 0.1M sodium phosphate pH 8.0 containing traces of cupric ions; air was bubbled through the mixture for 8 hours under mild shaking after which all thiol groups had been converted to gel bound disulfide groups. The product was stored in standard buffer.

Disulfide gel 2: 50 g suction dried thiol agarose (712 μmoles. HS-groups per gram dried product) was suspended in 100 mL sodium phosphate (pH 7.0, 0.1M) and potassium ferricyanide added in aliquots (0.1M, 1 mL) under shaking until the yellow colour persisted for at least 30 min. Then the gel was washed with sodium phosphate (pH 7.0, 0.1M), NaCl (1M), sodium acetate (pH 5.0, 0.2M).

Activation (Step (i))

Activation via disulfide agarose to thiolsulfonate agarose (to create —S—SO$_2$—): Hydrogen peroxide (30%) was added under continuous shaking and in aliquots to 15 g of thiol agarose or thiol agarose where the thiol groups previously had been oxidized to disulfides as described above (in both cases the agarose were suspended in 45 mL sodium acetate (0.2M, pH 5.0)); initially 1.8 mL and after 30 min. three more aliquots of 2.2 mL each at one hour intervals. The reaction was allowed to proceed for 24 hours, and then the gel was washed with acetic acid (0.1M) and stored in sodium acetate (0.2M, pH 5.0) at 4° C. Experiments were run with thiol agarose having 60–800 μmoles HS-groups per gram dried gel, and the result indicated that this range could give products carrying 30–400 μmoles of thiol reactive groups per gram dried gel. Measurement (i) of gel bound thiol groups after treatment of the reactive groups with excess of a low molecular thiol (reduced glutathione and beta-mercaptoethanol), and (ii) of the newly formed reactive groups after regeneration with H$_2$O$_2$-treatment in combination with (iii) sulfur and amino acid analysis of formed derivatives indicated that the majority of the gel bound reactive groups were of thiolsulfonate type (—S—SO$_2$—).

Activation of disulfide agarose to thiolsulfinate agarose (to create —S—SO—): 10 g of suction dried disulfide agarose (356 μmoles —S—S— groups per gram dried gel) was suspended in 20 mL of sodium acetate (0.2M, pH 5.0) containing 67 mg magnesium monoperoxy phtalate (MMP) and incubated under shaking for two hours at 50° C. The product was washed with sodium acetate (50 mM, pH 5,0), acetic acid (0.1M) and sodium acetate (0.2M, pH 5,0). The binding capacity for reduced glutathione was determined to 275 μmoles groups per gram dried gel product. The same set of analysis as described above for activation with H$_2$O$_2$ indicated that the reactive group is of thiolsulfinate type.

Activation of disulfide agarose to thiolsulfonate agarose (to create —S—SO$_2$—): The same procedure as previously but the amount of MMP was doubled. The binding capacity for reduced glutathione was determined. Analysis of the same type as described above for products formed with H$_2$O$_2$ oxidation indicated that although some of the gel bound reactive groups might be of thiolsulfinate type the majority of them were of the thiolsulfonate type (—S—SO$_2$—). The binding capacity for reduced glutathione was determined to 364 μmoles per gram dried gel derivative.

Activation of other thiol/disulfide-containing supports (to create —S—SO$_2$—): Thiolated forms of beaded cellulose, SEPHADEX G-75, and EUPERGIT were oxidized to thiolsulfonate agarose via disulfide formation in the same way as thiol agarose.

Optimization of the activation (step (i)): The effect of pH, hydrogen peroxide concentration and incubation time was studied for oxidation of thiol agarose (430 μmoles HS-groups per gram dried gel) to thiolsulfonate gel. After activation the thiolsulfonate gels were washed in acetic acid. (0.1M) and equilibrated in sodium acetate (0.2M, pH 5.0). The number of reactive groups was determined by the glutathione method.

(a) pH. Aliquots (6 g) of thiol agarose equilibrated in water were suspended in 15 mL of the following buffers: 0.2M sodium acetate pH 2.1, 0.2M sodium acetate pH 3.0, 4.0, 5.0, 6.0 and 0.2M sodium phosphate pH 6.0 and 7.0. Hydrogen peroxide (0.6 mL, 30%) was added to each suspension while shaking, and the reaction was allowed to proceed for 30 min. Then three aliquots of 0.73 mL each were added at one hours intervals and the incubation continued for 24 hours. The result indicated that there was a pH optimum at a slightly acidic pH within the range of pH 3.5 to 6. As pH is increased above 5 and approaches neutrality the degree of activation decreases drastically.

(b) H$_2$O$_2$. The concentration of hydrogen peroxide was studied in the range 1.0–6.5% final concentration. Incubation was performed for 24 hs. at 22° in sodium acetate (0.2M, pH 5.0). The result indicated that the hydrogen peroxide concentration was not very critical.

(c) Time. The incubation time was studied with 3.5% H$_2$O$_2$ at pH 5.0. Longer incubation times led to decreased coupling capacity. This was probably due to overoxidation leading to the formation of gel bound sulfonic acid groups. These results are valid for hydrogen peroxide. The use of other oxidizing agents and polymers may lead to other results, although it is believed that the pH dependency is essentially universal for peroxides.

Stability of thiolsulfonate gels: Activated gels of the types prepare above were stored under different conditions (pH, temperature, times and presence of agents such as azide ion, Tris buffer, halide ions, urea, guanidine.HCl etc.). The stability was satisfactory except for high pH (at pH 9 more than 50% of the active groups were lost after 72 hs.). The activated gels were also found to be stabile for at least one year when stored as a lyophilized powder at +4° C.

Coupling Reaction (Step (ii)):

Coupling kinetics as a function of pH (model substance reduced glutathione): Aliquots of thiolsulfonate agarose (2.5 g packed gel containing 10 μmoles —S—SO$_2$— groups per mL) were equilibrated at the pHs 3.5, 5.0 (0.1M sodium acetate), 6.0, 7.0, 8.0 and 8.5 (0.1M sodium phosphate). Each sample was mixed with 3.0 mL 15 mM glutathione (corresponding pH). Agitation was performed at regular intervals, and the rate of glutathione consumption followed; at different times aliquots of the supernatants (50 μL) were transferred from each sample to 3.0 mL 0.25 mM 2-PDS in sodium acetate (0.1M, pH 8.0). The absorbance at 343 nm was measured and plotted as a function of incubation time. The rate of glutathione consumption was determined as $t^{1/2}$ (half-life time). Controls for the spontaneous glutathione oxidation at each pH were run using 2.5 mL of buffer instead of gel. No reaction could be detected at pH 3.5. At pH 5.0 immobilization occurred at a reasonable rate, and further increase in pH speeded up the reaction. Above pH 8 the reaction was too fast to be measured. This result together with a decreased stability for the reactive group (—S—SO$_2$—) at alkaline pH propose an optimal pH for step (ii) within 3.5–9, preferably 5–9, i.e the same as normal thiol-disulfide exchange reactions.

Coupling of Specific Compounds (Step (ii)):

(a) Thiols that are stabilized by thiol-thione tautomerism to the thione forms (mainly aromatic thiols): These thiols are known to react poorly with alifatic disulfides. 0.5 mL of 2-thiopyridone (50 mg/mL in methanol) was added while mixing to 2 g of thiolsulfonate agarose that had been suction dried, equilibrated and suspended in sodium acetate (0.2M, pH 5.0). Incubation was performed at 22° C. for 16 hours. The amount of 2-pyridyl disulfide groups bound to the gel was determined after washing the gel and treatment with 10 mL of 50 mM DTT (dithiotreitol) in sodium phosphate (0.1M, pH 8.0) and measurement of the released 2-thiopyridone (Biochem.J. 173(1978)pp723-). The result indicated that the thiolsulfonate groups react quantitatively with 2-thiopyridone.

(b) Low molecular weight thiols:

Beta-mercaptoethanol: Beta-mercaptoethanol (20 mL, 10 mM) in sodium phosphate (0.1M, pH 8.0)) was added to suction dried thiolsulfonate gel (12 g) that had been washed in distilled water. The reaction was allowed to proceed for 1 hour under shaking. The gel was then washed with distilled water, equilibrated in 20 mL ethanol (95%). Sulfur analysis before and after reaction showed that the thiolsulfonate groups reacted quantitatively with beta-mercaptoethanol. Titration of the treated gel and of the untreated thiolsulfonate gel (reference) with NaOH. (0.025N) and Bromophenol Blue (0.1%) as indicator showed that acidic groups with pKa below 2 was created as a consequence of the treatment with beta-mercaptoethanol. From knowledge of the behaviour of low molecular weight thiolsulfonates when treated with thiols and the pKa values for sulfinic acids the gel bound acidic group formed most likely is a sulfinic acid group. This titration procedure is similar to a method for quantitation of sulfinic acid (Barnard et al. Anal. Chim. Acta 20(1959) pp540-).

Reduced glutathione: See above under immobilization kinetics and analyses of thiol binding capacity. Amino acid and sulfur analyses of the glutathione gels produced indicated that —S—SO$_2$— groups and glutathione reacted in stoichiometric amounts. For —S—SO— the yield appeared lower.

(c) Thiol-containing proteins: By applying the optimal conditions given above, beta-galactosidase from *E. Coli*, urease from jack bean and alcohol dehydrogenase from baker's yeast (all three enzymes were from Sigma Chem. Co. St. Louis. Mo. U.S.A. and all having native exposed thiol groups) were immobilized on thiolsulfonate agarose (250 μmoles of —S—SO$_2$— groups per gram dried gel product). Depending on the amount of enzymes used in the coupling reaction, derivatives with 20–200 mg protein per gram dried derivative could be prepared. Low load derivatives showed that about 50–70% of the applied enzyme activity was conserved after the immobilization. The thiol-protease papain was also immobilized, however, with loss of activity since its only thiol group which is essential for its protease activity was utilized in the binding to the gel. Bovine serum albumin (BSA) did not react in spite of its content of a free thiol group. This most likely depends on its free thiol group being sterically unavailable since it is located inside a hydrophobic pocket. This idea is supported by the fact that the same type of albumin after having been denatured reacted more easily and bound to some extent to the gel. After introduction of four de novo thiol groups per mole BSA, it was also possible to bind large amounts of bovine serum albumin to the thiolsulfonate gel. The inertness of native BSA to react with the derivatives of the invention is contrary to what previously has been found for reaction of BSA with gels carrying reactive disulfides such as 2-pyridyl disulfide groups. Hence the solid supports of the invention provide reactive groups having new selectivities for reactions with thiol compounds.

Similarly it was possible to immobilize sweet potato beta-amylase after thiolation.

The capacity of binding thiolated BSA was essentially proportional to the capacity for binding reduced glutathione, although only 2% of the reactive groups were utilized for protein binding, most probably because of steric reasons.

Release of Bound Thiol Compounds and Regeneration of the Activated Gel.

30 g (suction dried) gel derivative (glutathione or protein derivative) was reduced with 50 mM DTT in sodium phosphate (0.1M, pH 8.0) for two hours under shaking. The result was that essentially all of the bound thiol compounds were released and could be washed away as demonstrated by e.g. amino acid analysis before and after the treatment. After careful washing of the gel to remove all traces of DTT the gel was regenerated by oxidation as described above.

(a) Thiolsulfonate agarose: In this case the regeneration was performed with $H_2O_2$. Reactivity towards glutathione and binding capacity for thiolated BSA was determined after regeneration. The release, regeneration and coupling cycles were repeated several times. The result indicated that for each cycle the capacity decreased with about 50%. This figure is compatible with the proposed activated structure being a thiolsulfonate group.

(b) Thiolsulfinate agarose: In the case of thiolsulfinate agarose the regeneration was performed with magnesium monoperoxy phtalate (MMP) as described above. The result showed that nearly 100% of the capacity was recovered after each regeneration.

Preliminary Experiments with Disulfide-Containing Proteins Used as the Polymer and 2-Thiopyridone as HS—R (Steps (i) and (ii):

Bovine serum albumin (BSA): 1 mL aliquots of BSA (200 mg/mL, 3.03 μmoles/mL) dissolved in sodium acetate (0.2M, pH 5.0) were separately incubated with 1.0 mL of MMP solutions (50, 25, 20, and 12.5 μmoles/mL in sodium acetate (0.2M, pH 5.0)) at 37° C. for 90 min. Protein precipitation was observed for the two highest concentrations of MMP. The reaction was stopped by gel filtration (PD-10 columns; medium 0.2M sodium acetate pH 5.0; Pharmacia AB. Sweden). The void material containing the activated protein (1.0 mL eluate; samples with no precipitation were selected) was then incubated with 2-thiopyridone (50 μL of a 0.5M solution in methanol) for one hour at room temperature. After gel filtration (PD-10), the absorbance of the void fraction at 280 nm was determined; and then 2-thiopyridone were released by treatment with DTT, and the absorbance of the solution measured at 343 nm. A relationship of 1.5 μmoles reactive groups per mole of μmole protein was determined (the protein concentration was estimated from the determination at 280 nm with correction for the contribution from pyridyl disulfide groups). Conclusion: By use of a reasonable excess (up to 6.6 μmoles per μmoles protein) and specified conditions, thiol reactive groups could be introduced into BSA, but with larger excess the BSA precipitated.

Gamma globulin (Fraction II, from rabbit): 1.0 mL alilquots of gamma-globulin (100 mg/mL, 0.625 μmoles/L) dissolved in sodium acetate (0.2M, pH 5.0) were incubated with 0.11 and 0.31 mL of MMP solution (20 μmoles/L) in the same buffer. After treatment with 2-thiopyridone and measurement as described for BSA, 3.6 μmoles reactive groups per μmoles gamma globulin could be detected in both cases. Higher concentrations of oxidation agent produced denaturation of gamma globulins and precipitation during the incubation period.

I claim:

1. Method for the immobilization of an organic thiol compound, HS—R, in which R is an organic residue, to a water-insoluble polymer of non-polypeptide structure exhibiting a disulfide (—S—S—) group directly bound to a saturated carbon atom at each of its sulphur atoms, characterized in the steps that:

(i) said polymer is contacted with an oxidation agent in such an amount and of such a kind that it is capable of transforming said disulfide group (—S—S—) to an oxidized disulfide group capable of reacting with thiol groups, whereupon (ii) the polymer obtained in step (i) exhibiting one or more oxidized disulfide groups is contacted with the organic thiol compound HS—R under conditions allowing reaction to the formation of one —S—S—R group and one —SO$_n$(H) group per disulfide oxide group that undergoes the reaction where n is 1 or 2.

2. Method according to claim 1 wherein said oxidation agent is a peroxide (—OO—) selected from the group consisting of inorganic peroxides having the general formula X—OO—X', where X and X' are hydrogen or a metal ion, and peroxides complying with the formula X—OO—X', where X and X' have the same meaning as previously given except that at least one of them is an organic residue having a carbon atom attached directly to the peroxy group (—OO—).

3. Method according to claim 2 wherein said peroxide is an organic peroxide in which at least one of X and X' is an organic residue that provides a carbonyl group (—CO—) attached directly to the peroxy group.

4. Method according to claim 3 wherein the organic residue provides an aromatic ring that is attached directly to said carbonyl group.

5. Method according to claim 3 wherein said peroxide, in addition to a group having a carbonyl attached directly to the peroxy group, also exhibits a —CO—O— group at a distance of two or three carbon atoms from said carbonyl group.

6. Method according to claim 5 wherein the peroxide is a metal salt of a peroxy phthalic acid.

7. Method according to claim 1 wherein the disulfide group (—S—S—) bound directly to a saturated carbon atom at each of its sulphur atoms and present in the polymer that is to be used in step (i) has been created in a step preceding step (i) by oxidizing the thiol groups of a polymer carrying thiol groups.

8. Method according to claim 1 wherein the oxidized disulfide group is a —S—SO$_n$— group, in which n is equal to 1 or 2 and wherein step (i) is performed selectively to the stage where n essentially equals 1 or 2.

9. Method according to claim 1 wherein said compound HS—R is selected from the group of compounds consisting of proteins.

10. Method according to claim 1 wherein said compound HS—R is a compound capable of participating in biospecific affinity reactions.

11. Method for the immobilization of an organic thiol compound, HS—R, in which R is an organic residue, to a polymer exhibiting a disulfide (—S—S—) group directly bound to a saturated carbon atom at each of its sulphur atoms characterized in the steps that:

(i) said polymer is contacted with an oxidation agent in such an amount and of such a kind that it is capable of selectively transforming said disulfide group (—S—S—) to a —S—SO$_n$— group where n is essentially 1 or 2, whereupon (ii) the polymer obtained in step (i) exhibiting one or more —S—SO$_n$— groups is contacted with the organic thiol compound HS—R under conditions allowing reaction to the formation of one —S—S—R group and one —SO$_n$(H) group per —S—SO$_n$— group that undergoes the reaction, with the proviso that the polymer carrying the disulfide group is not a wool textile fiber.

12. Method according to claim 11 wherein said oxidation agent is a peroxide (—OO—) selected from the group consisting of inorganic peroxides having the general formula X—OO—X', where X and X' are hydrogen or a metal ion, and organic peroxides complying with the formula X—OO—X', where X and X' have the same meaning as previously given except that at least one of them is an organic residue having a carbon atom attached directly to the peroxy group (—OO—).

13. Method according to claim 12 wherein said peroxide is an organic peroxide in which at least one of X and X' is an organic residue that provides a carbonyl group (—CO—) attached directly to the peroxy group.

14. Method according to claim 13 wherein the organic residue provides an aromatic ring that is attached directly to said carbonyl group.

15. Method according to claim 13 wherein said peroxide, in addition to the carbonyl group attached directly to the peroxy group, also exhibits a —CO—O— group at a distance of two or three carbon atoms from said carbonyl group.

16. Method according to claim 15 wherein the peroxide is a metal salt of a peroxy phthalic acid.

17. Method according to claim 11 wherein the disulfide group (—S—S—) bound directly to a saturated carbon atom at each of its sulphur atoms and present in the polymer that is to be used in step (i) has been created in a step preceding step (i) by oxidizing the thiol groups of a polymer containing thiol groups.

18. Method according to claim 11 wherein said polymer is insoluble in water and of non-polypeptide structure.

19. Method according to claim 11 wherein said compound HS—R is selected from the group of compounds consisting of proteins.

20. Method according to claim 11 wherein said compound HS—R is a compound participating in biospecific affinity reactions.

* * * * *